United States Patent
Wiggers

(10) Patent No.: US 9,925,394 B2
(45) Date of Patent: Mar. 27, 2018

(54) AUTOMATIC HEALTH DETECTION FOR MOTION AXES IN MEDICAL LINEAR ACCELERATORS

(75) Inventor: Robert T. Wiggers, Belmont, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 808 days.

(21) Appl. No.: 13/156,290

(22) Filed: Jun. 8, 2011

(65) Prior Publication Data

US 2012/0314844 A1 Dec. 13, 2012

(51) Int. Cl.
*G05B 23/02* (2006.01)
*A61N 5/10* (2006.01)

(52) U.S. Cl.
CPC .................. *A61N 5/1075* (2013.01)

(58) Field of Classification Search
USPC ....... 318/565, 687, 135, 437, 638, 162, 164; 388/904
See application file for complete search history.

(56) References Cited

U.S. PATENT DOCUMENTS

| 5,676,162 | A * | 10/1997 | Larson, Jr. | A61M 1/101 128/899 |
| 5,898,288 | A * | 4/1999 | Rice | G05B 19/21 318/400.12 |
| 7,144,094 | B2 * | 12/2006 | Chung | B41J 19/202 347/19 |
| 7,934,657 | B2 * | 5/2011 | Martenson | G01D 5/24409 235/454 |
| 2003/0201747 | A1 * | 10/2003 | Chaffee | 318/630 |
| 2005/0258688 | A1 * | 11/2005 | Miyamoto | F16C 29/06 310/12.09 |
| 2007/0074347 | A1 * | 4/2007 | Coppens | A61B 6/0442 5/600 |
| 2008/0301872 | A1 * | 12/2008 | Fahrig | A61B 6/0457 5/81.1 R |
| 2009/0140748 | A1 * | 6/2009 | Lindsey | G01R 31/02 324/538 |
| 2011/0074288 | A1 * | 3/2011 | Mohr | H05H 7/00 315/5.41 |
| 2011/0075815 | A1 * | 3/2011 | Brown et al. | 378/125 |

FOREIGN PATENT DOCUMENTS

JP 07063885 A * 3/1995
JP 407063885 A * 3/1995

* cited by examiner

*Primary Examiner* — Eduardo Colon Santana
*Assistant Examiner* — Iftekhar Mustafa
(74) *Attorney, Agent, or Firm* — Houst Consulting

(57) ABSTRACT

In a method of detecting the health of a motion axis in a radiation system including a motor operable to move a load between a first end and a second end, data on an electrical parameter of the motor is collected as the motor moves in the certain range. At least one indicator of the electrical parameter including a maximum, a minimum, an average, and a standard deviation of the electrical parameter is determined and compared with a provided value or range of values indicative of the health of the axis. The health of the motion axis is determined using the comparison of the at least one indicator and the provided value or range of values.

17 Claims, 10 Drawing Sheets

AUTOMATIC HEALTH DETECTION FOR MOTION AXES IN MEDICAL LINEAR ACCELERATORS

CROSS REFERENCE TO RELATED APPLICATIONS

This application is related to the following applications, the disclosures of all of which are incorporated herein by reference in their entirety.

U.S. application Ser. No. 12/641,538, filed Dec. 18, 2009 and entitled "Homing and Establishing Reference Frames for Motion Axes in Radiation Systems."

U.S. application Ser. No. 12/551,059, filed Aug. 31, 2009 and entitled "Target Assembly with Electron and Photon Windows."

U.S. application Ser. No. 12/568,619, filed Sep. 28, 2009 and entitled "Beam Filter Positioning Device."

U.S. application Ser. No. 12/568,621, filed Sep. 28, 2009 and entitled "Energy Switch Assembly for Linear Accelerators."

BACKGROUND

This disclosure relates in general to radiation systems and methods and in particular to methods and systems for automatic health detection for motion axes in medical linear accelerators (MLAs).

Radiation systems such as medical linear accelerators include various motion axes that operate coordinately to produce and deliver treatment beams and to position patients and other units such as imaging devices. A motion axis may include a motor operable to move a device in a linear and/or an angular direction, and one or more feedback devices that provide position and/or velocity information about the axis. There are instances that a motor may slip, an axis may have wearing components which are nearing the end of their life, feedback devices and/or sensors may fail, slip, or move, or an axis may be serviced without being properly calibrated prior to use. Any of these problems constitute safety hazards and may cause a mistreatment or undesirable machine shutdown.

Therefore, there is a need for a method and system for detecting the health of motion axes in a medical linear accelerator. There is a need for increasing the overall operating capability of a medical linear accelerator and preventing unexpected shutdowns of the machine.

SUMMARY

Medical linear accelerators using computer controlled motion axes to move various devices in a prescribed range of travel are provided. Also provided are methods and systems for health detection of motion axes in a medical linear accelerator. Other embodiments are described further herein.

BRIEF DESCRIPTION OF THE DRAWINGS

These and various other features and advantages will become better understood upon reading of the following detailed description in conjunction with the accompanying drawings and the appended claims provided below, where:

DETAILED DESCRIPTION

Various embodiments of machine health systems are described. It is to be understood that the invention is not limited to the particular embodiments described as such which may, of course, vary. An aspect described in conjunction with a particular embodiment is not necessarily limited to that embodiment and can be practiced in any other embodiments. For instance, while various embodiments are described in connection with medical linear accelerators, it will be appreciated that the invention can also be practiced in other electromagnetic apparatuses and modalities. It is also to be understood that the terminology used herein is for the purpose of describing particular embodiments only, and is not intended to be limiting since the scope of the invention will be limited only by the appended claims, along with the full scope of equivalents to which such claims are entitled.

In addition, various embodiments are described with reference to the figures. It should be noted that the figures are not drawn to scale, and are only intended to facilitate the description of specific embodiments. They are not intended as an exhaustive description or as a limitation on the scope of the invention.

As used herein, the term "motion axis" or "axis" refers to a mechanism that is operable to move an object in a direction. For example, a "linear axis" refers to a mechanism that is operable to move an object in a linear direction. A "rotational axis" refers to a mechanism that is operable to rotate an object in an angular direction. By way of example, an axis may include a motor, a load drivingly coupled to the motor, and one or more feedback devices that provide position and/or velocity signals. In some embodiments, an axis may be a servo controlled pneumatically driven mechanism such as a pneumatically driven linear or rotary device with dual chambers.

As used herein, the term "hardstop" refers to a fixed structural feature of a system that defines an end-of-travel of a motion axis.

Figure 1:
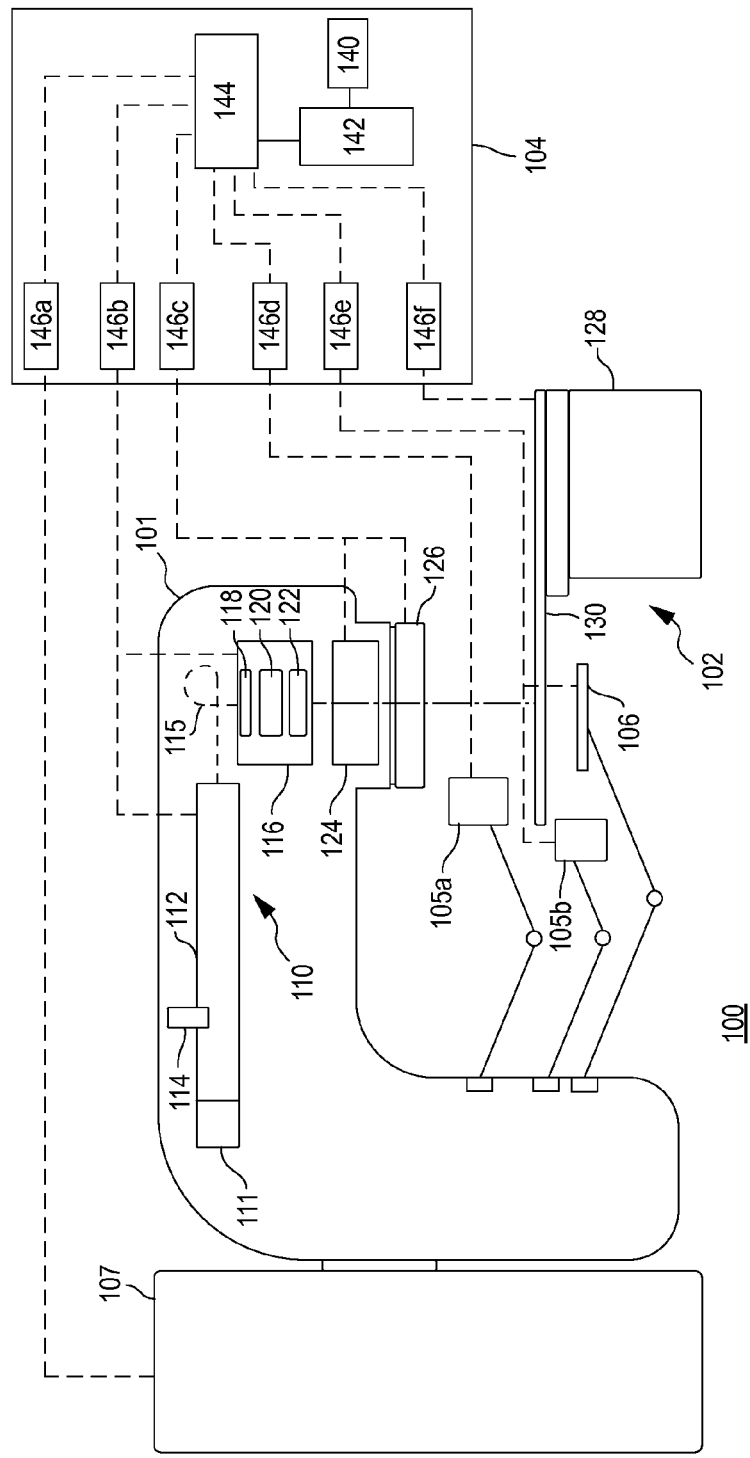
FIG. 1 is a schematic representation of an exemplary linear accelerator in accordance with some embodiments.

FIG. 1 is a schematic representation of an exemplary linear accelerator system 100 that can embody the principle of the disclosure. The accelerator system 100 may include various axes that are operable to move various devices in producing and delivering treatment beams or in positioning a patient or devices for imaging, etc. The system 100 may include a gantry 101, a patient support 102, a control system 104, and optionally various devices for image acquisition 105a, 105b, 106. The gantry 101 may be rotatably supported by a stand 107 and contain various devices for beam generation and collimation. For example, an accelerator 110 may include an electron gun 111 configured to produce and inject electrons into an accelerator guide 112, which may have a plurality of accelerating cavities coupled with pulsed microwave energies. An energy switch assembly 114 may be mounted to the accelerator guide 112 operable to assist in modulating the energy levels of output electron beams. The energy switch assembly 114 may be moved with a linear axis to position a probe in a side cavity of the accelerator guide 112. The insertion of a probe into the side cavity may change the geometry of the cavity, thereby altering the electromagnetic fields which couple to the side cavity and adjacent accelerating cavities. This may in turn alter the energy level of the electron beam downstream from the energy switch assembly 114. By moving and precisely positioning a probe in a side cavity of the accelerator guide, the energy level of an output beam can be controlled.

The output electron beam 115 may be directed to a treatment head 116 which may house various device assemblies configured to produce, shape, or monitor treatment beams. For example, a target assembly 118 may be moved with a linear and/or a rotational axis to position a target relative to a beam line. In a photon mode operation, a target may be positioned in the beam path for producing X-ray radiation. In an electron mode operation, the target may be moved out of the beam path to allow an electron beam to pass unimpeded.

Beam filter assembly 120 may support one or more photon flattening filters and one or more electron scattering foils. The beam filter assembly 120 may be moved with one or more motion axes to position a photon flattening filter or an electron scattering foil relative to the beam path. For instance, two linear axes may move the beam filter assembly 120 e.g. in X-Y directions to position a photon flattening filter or an electron scattering foil. Alternatively, one linear axis and one rotational axis, or two rotational axes may be used to move the beam filter assembly 120 in positioning a photon flattening filter or an electron scattering foil. By way of example, the beam filter assembly 120 may include a stage and a filter-foil plate supported by the stage configured to support one or more photon flattening filters and one or more electron scattering foils. A linear axis may move the stage and thus the filter-foil plate supported by the stage in a linear direction. A rotational axis, which may be supported by the stage, may rotate the filter-foil plate in an angular direction.

Ion chamber assembly 122 may be moved with a linear axis or rotational axis to position an ion chamber relative to the beam path for measuring the parameters of a treatment beam such as beam energy, dose distribution, and dose rate etc. In a photon mode operation, the ion chamber may be positioned under a photon flattening filter for measuring the parameters of a radiation beam. In an electron mode operation, the ion chamber may be positioned under an electron scattering foil in the beam centerline for detecting the parameters of an electron beam.

While not shown in FIG. 1, the treatment head 116 may include other devices or assemblies which may be moved with other motion axes, or alternatively, moved by one or more motion axes that are described above. For example, the treatment head 116 may further include a field light assembly that may be operable to move a light source and/or a mirror to provide simulation of treatment field. The beam filter axes 120 or ion chamber axis 122 described above may also move other functional components. For instance, the ion chamber axis may also move a backscatter filter to block backscattered radiation, which may have unwanted effects on the calibration of the ion chamber.

Collimation assembly 124 may include upper collimator jaws and lower collimator jaws each of which may be moved by a linear or rotational axis to provide secondary collimation. The linear or rotational axes for the lower or upper collimator jaws may be independently controlled. The upper and lower collimator jaws may be housed in an enclosure and rotated by a rotational axis. Multileaf collimator (MLC) 126 may include a plurality of individual leaves each of which may be moved with a linear axis. By moving individual leaves to selected positions in a controlled manner, the size and shape of the treatment beam can be controlled.

Treatment couch 102 on which a patient can be supported or positioned may include a base 128 and a couch top 130. Linear axes may move the couch top 130 in the lateral (x-axis) and/or longitudinal (y-axis) directions. Linear axis may also move the base 128 vertically so that the couch top 130 may be moved in the vertical directions (z-axis). Rotational axes may rotate the couch 102 about an isocenter to provide a different couch angle relative to the radiation source, or rotate the couch top 130 to provide pitch, yaw, and/or roll rotation of the couch top 130.

The accelerator system 100 may optionally include devices for imaging such as imaging source 105a, image acquisition devices 105b and 106 for use with keV or MV sources. Various linear and/or rotational axes may be used to move the sources and image acquisition devices in linear and/or angular directions.

Control system 104 controls the operation of the linear accelerator system 100, preferably with a computer user interface 140. The control system 104 may include a processor 142 such as e.g. a digital signal processor, a field programmable gate array, a central processing unit, or a microprocessor. The processor 142 may execute programs and generate signals for operation of the motion axes and other devices or assemblies of the accelerator system. In some embodiments, the control system 104 may include a main control unit 144 which may supervise or regulate a plurality of controllers or nodes or sub-nodes 146a-146f. Each controller or node 146a-146f may be configured to control one or more motion axes for moving or positioning one or more devices. Responsive to the commands from a controller, one or more motion axes may move one or more devices or assemblies such as an energy switch, a target, a beam filter, field light units, a treatment couch, imaging units etc. in a controlled and automatic manner based on a plan or routine, or based on the input from a user. The controller 146a-146f may receive signals from position feedback devices, sensors, or from other devices such as the ion chamber, and generate commands for adjustment when necessary. For example, based on the beam parameter signals provided by the ion chamber 122, the control system 104 may recalculate and generate commands for adjustment to various motion axes. The motion axes may respond and adjust automatically the positions e.g. of the energy switch, target, beam filters, or collimators etc.

Figure 2:
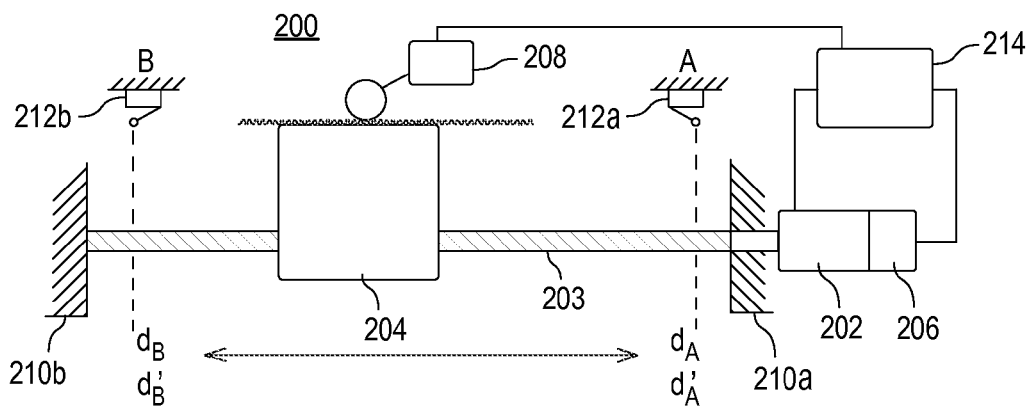
FIG. 2 is a schematic representation of an exemplary linear axis in accordance with some embodiments.

FIG. 2 illustrates an exemplary linear motion axis 200 which can embody the principle of the disclosure. The linear motion axis 200 may include a motor 202, a load 204 drivingly coupled to the motor 202, and one or more feedback devices 206, 208. The load 204 may be an energy switch assembly, a target assembly, a beam filter assembly, an ion chamber assembly, a collimation assembly, or an MLC assembly. The load 204 may also be a treatment couch, or various other devices or units as illustrated in FIG. 1, or a body supporting one or more of the described devices or assemblies. The feedback device 206 may be coupled to the motor shaft to provide feedback signals which may be used to measure the position and/or velocity of the motor. The feedback device 208 may be coupled to the load 204 to provide feedback which may be used to measure the position and/or velocity of the load. In some embodiments, one or more feedback devices may be coupled to the motor 202 and/or one or more feedback devices coupled to the load 204 respectively to provide feedback on the position and/or velocity of the motor and the load respectively. In some embodiments, two or more feedback devices may be coupled to the motor 202 each of which may independently provide feedback on the position and/or velocity of the motor. In some embodiments, two or more feedback devices may be coupled to the load 204 each of which may independently provide feedback on the position and/or velocity of the load. The motor 202 and feedback devices 206, 208 may be electrically coupled to a controller 214. Structural features 210a, 210b define the end-of-travel of the linear axis 200 and the range of travel of the axis. In some embodiments, the structural features 210a, 210b are fixed structures or hardstops the locations of which will not be changed for the life of the system. In some embodiments, the linear axis 200 may optionally include limit switches or limit sensors 212a, 212b located near the hardstops 210a, 210b. When triggered, the limit switches 212a, 212b may signal the controller 214 that the axis is approaching an end of travel. The controller 214 may then reduce the axis speed and lower the peak torque capacity of the motor to avoid collision damage to the axis and increase positioning accuracy.

Figure 3:
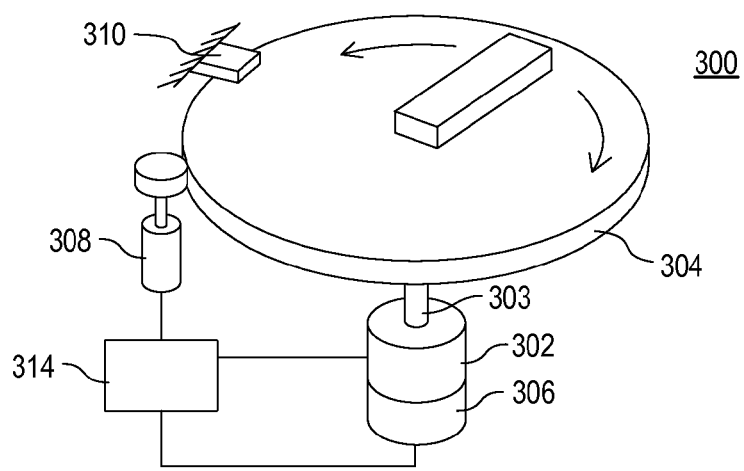
FIG. 3 is a schematic representation of an exemplary rotational axis in accordance with some embodiments.

FIG. 3 illustrates an exemplary rotational motion axis 300 which can embody the principle of the disclosure. The rotational motion axis 300 may include a motor 302, a load 304 drivingly coupled to the motor 302, and one or more feedback devices 306, 308. The load 304 may be an energy switch assembly, a target assembly, a beam filter assembly, an ion chamber assembly, a collimation assembly, or an MLC assembly. The load 304 may also be a treatment couch, or various other devices or units as illustrated in FIG. 1, or a body supporting one or more of the described devices or assemblies. The feedback device 306 may be coupled to the motor 302 to provide feedback signals which may be used to measure the position and/or velocity of the motor. The feedback device 308 may be coupled to the load 304 to provide feedback signals which may be used to detect the position and/or velocity of the load. In some embodiments, one or more feedback devices may be coupled to the motor 302 and/or one or more feedback devices coupled to the load 304 respectively to provide feedback on the position and/or velocity of the motor and the load respectively. In some embodiments, two or more feedback devices may be coupled to the motor 302 each of which may independently provide feedback on the position and/or velocity of the motor. In some embodiments, two or more feedback devices may be coupled to the load 304 each of which may independently provide feedback on the position and/or velocity of the load. The motor 302 and feedback devices 306, 308 may be electrically coupled to a controller 314. Structural features 310 define the end-of-travel of the linear axis 300 and the range of travel of the axis. In some embodiments, the structural features 310 are fixed structures or hardstops the locations of which will not be changed for the life of the system. As used herein, the structural features 310 can be two independent or separate hardstops, or one hardstop with two hard contact surfaces. In some embodiments, the rotational axis 300 may optionally include limit switches or limit sensors (not shown in FIG. 3) located near the hardstops, which when triggered signal the controller 314 that the axis is approaching an end of travel. The controller 314 may then reduce the axis speed and lower the peak torque capacity of the motor to avoid collision damage to the axis and increase positioning accuracy.

The motors 202, 302 are preferably a servo motor such as brush servo motors, brush-less servo motors, stepper motors, linear motors, servo-controlled dual-cylinder pneumatic/hydraulic drives, or any other suitable motors. Various motors are known in the art and their detail construction is omitted herein for clarity of the description of the disclosure. The motors 202, 302 may be drivingly coupled to the load via various suitable means. For example in FIG. 2, a ball screw 203 may engage with the load 204 and be coupled to the motor 202 via a coupler. In operation the motor 202 may rotate the ball screw 203, which in turn translates the load 204 in a linear direction. In FIG. 3, a shaft 303 may engage with the load 304 e.g. via a bearing assembly and be coupled to the motor 302 via a coupler. The motor 302 rotates the shaft 303, which in turn rotates the load 304 in an angular direction. Any other means of coupling known in the art may be used to transmit the driving force from the motor to the load. For example, timing belt, pulleys, rollers, nuts, guides and various other units may be used to drivingly couple the load to the motor.

The feedback devices 206, 306 may be relative, incremental, or absolute feedback devices. The feedback devices 206, 306 and the controller keep track of the overall absolute positions throughout the range of motion of the axis. For example, the feedback devices 206, 306 can be optical encoders, magnetic encoders, transducer encoders such as resolvers or linear varying differential transducers (LVDT), and capacitive encoders. The feedback devices 206, 306 can be linear or rotary encoders, absolute or incremental encoders. Various encoders, resolvers, Hall sensors, tachometers and potentiometers are known in the art and commercially available and thus their detail construction is not described herein. In general, a rotary encoder is a position feedback device that sends a digital pulse as exact angular increments about a single revolution. An incremental encoder can also send an index pulse at every revolution at the same rotational angle of the device. A resolver is a rotary position feedback device that gives absolute position through one full revolution. The voltage value generated when a resolver is rotated to exactly 0 degree is called null voltage. A series of Hall sensors may be used e.g. in a brushless electric motor to detect the position of the permanent magnet. Hall sensors are typically used for motor commutation, but a system of Hall sensors, for the purpose of homing, can be considered a positioning device since it gives distinct position information of the motor per revolution. A tachometer is an analog device which returns an electrical signal (voltage) as proportional to rotation speed. A tachometer is a feedback for shaft rotational velocity. A potentiometer is an analog device which returns an electrical signal (resistance) as a function of rotation angle. A potentiometer is an angular positioning sensor. By way of example, when a feedback device such as an encoder or a resolver is coupled to a motor, the position of the rotating motor shaft can be ascertained and the position of the load connected to the motor shaft calculated by counting pulses or reading the voltages in the direction of rotation and tracking the revolutions of the encoder or resolver. For example, when a home or reference position has been established for an axis, the controller may capture the angle of the feedback device and resets the device at the reference position. As the axis is commanded to move from the reference position, the controller receives subsequent pulses or voltage signals from the feedback device each of which corresponds to a predetermined unit change in angular or rotational position of the motor. As the axis includes a mechanism that translates the motor shaft rotation into linear or angular movement of the load, the current position of the load can be calculated based on the current angle of the feedback device and the total revolutions of the device tracked and recorded by the controller. It should be noted that a linear motor and a linear encoder or any combination of suitable motors and feedback devices can be used.

The controller 214, 314 may include a memory, a processor, and an input and output (I/O) device. The memory stores programs or algorithms including servo loop control algorithms and other programs for operation of various motion axes. Dimensional data of fixed structural features or hardstops in the radiation system may be provided to the controller and stored in the memory. For example, the value of distance between the hardstops for a linear axis, or the value of angle between hardstops for a rotational axis may be provided to and stored in the controller's memory. The processor executes the programs and generates commands for operation of the motion axes. The controller receives signals from the feedback devices and sensors and sends signals such as voltage and current output to command the motor via the input and output (I/O) device or system.

The controller 214, 314 may be programmed to execute a servo loop algorithm such as a torque control, velocity control or position control etc., and modify the current or voltage output to the motor based on the feedback from the feedback devices. For instance, based on the actual feedback position and the desired position of the motor or the load, the controller may produce a power output required to drive the motor or the load to a desired position. The controller 214, 314 may be programmed to monitor the magnitude change pattern of the motor's electrical parameters such as the motor current and back EMF etc. during the motion of the axis toward a hardstop, and compare the monitored value with a predetermined value stored in the controller. The controller 214, 314 may monitor current using electronic circuitry designed to allow direct reading of the current sent to the motor. The controller 214, 314 may also be programmed to monitor the motor feedback device or load feedback device during the motion of the axis toward a hardstop. The velocity of the motor or the load may be measured by monitoring back EMF or the feedback devices coupled to the motor or load and compared with a predetermined value stored in the controller. Various methods are known by which the controller 214, 314 can determine velocity from feedback devices. For example, when position-based feedback devices such as encoders, resolvers, a series of Hall sensors, or potentiometers are used, the controller 214, 314 may compute velocity from the position difference over a given time period. With velocity-based feedback devices such as a tachometer, the controller 214, 314 may compute velocity from the direct feedback value times a given proportionality constant. The controller 214, 314 can also determine velocity using the motor's electronic characteristic of back EMF. The controller 214, 314 may include electronic circuitry for determining both the voltage supplied to the motor and the return voltage. By comparing these voltages along with known motor constants, the controller 214, 314 can compute the motor velocity. In cases where the system includes limit switches which signal the controller that the axis is approaching its end of travel, the controller 214, 314 may also be programmed to reduce the axis speed and lower the peak torque capacity of the motor to avoid collision damage to the axis and improve the accuracy of measurement. The controller 214, 314 may be programmed to execute a homing routine to establish a home position for an axis and record the home position. The controller 214, 314 may capture signals from the feedback devices or sensors which are indicative of the current position of the motor or the load, and calculate the current position of the motor or the load with reference to the home position that has been established. The controller 214, 314 may be programmed to generate alert or warning messages if it determines that certain faults occur.

The motor's electrical parameters such as the motor current and back EMF etc. can be monitored during the motion of the axis. The motor current may maintain at a generally constant magnitude during certain range of motion of the axis before hitting a hardstop. There may be small variation of the current magnitude due to the non-uniform friction of the axis components such as screws, belts or bearings etc. For example, the motor current may have an average value, a maximal value, a minimal value, and a standard deviation during certain range of motion of the axis. These and other indicators are generally characteristic of a motion axis and sometime referred to as baseline values of the motion axis. The baseline values of a motion axis can be ascertained when the axis is built at factory or calibrated prior to the operation of the axis.

Figure 4:
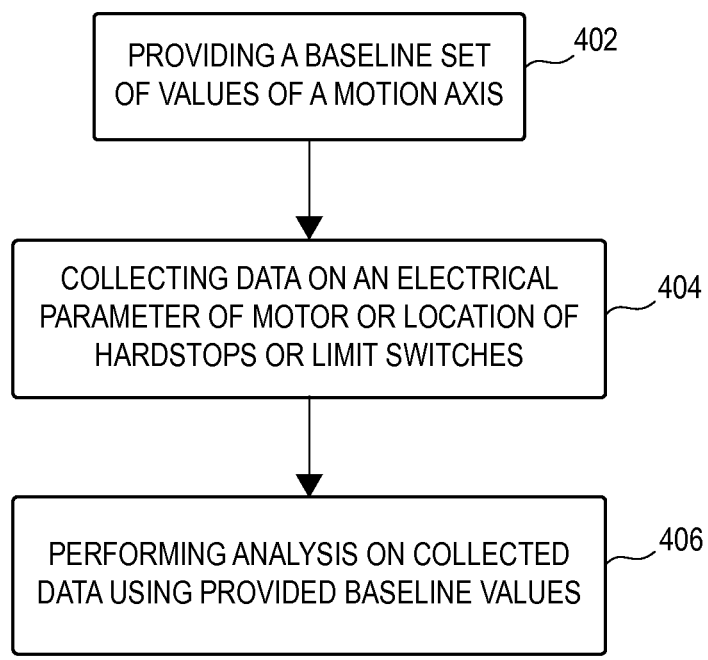
FIG. 4 is a flow chart illustrating an exemplary method for detecting the health of a motion axis in accordance with some embodiments.
Figure 5:
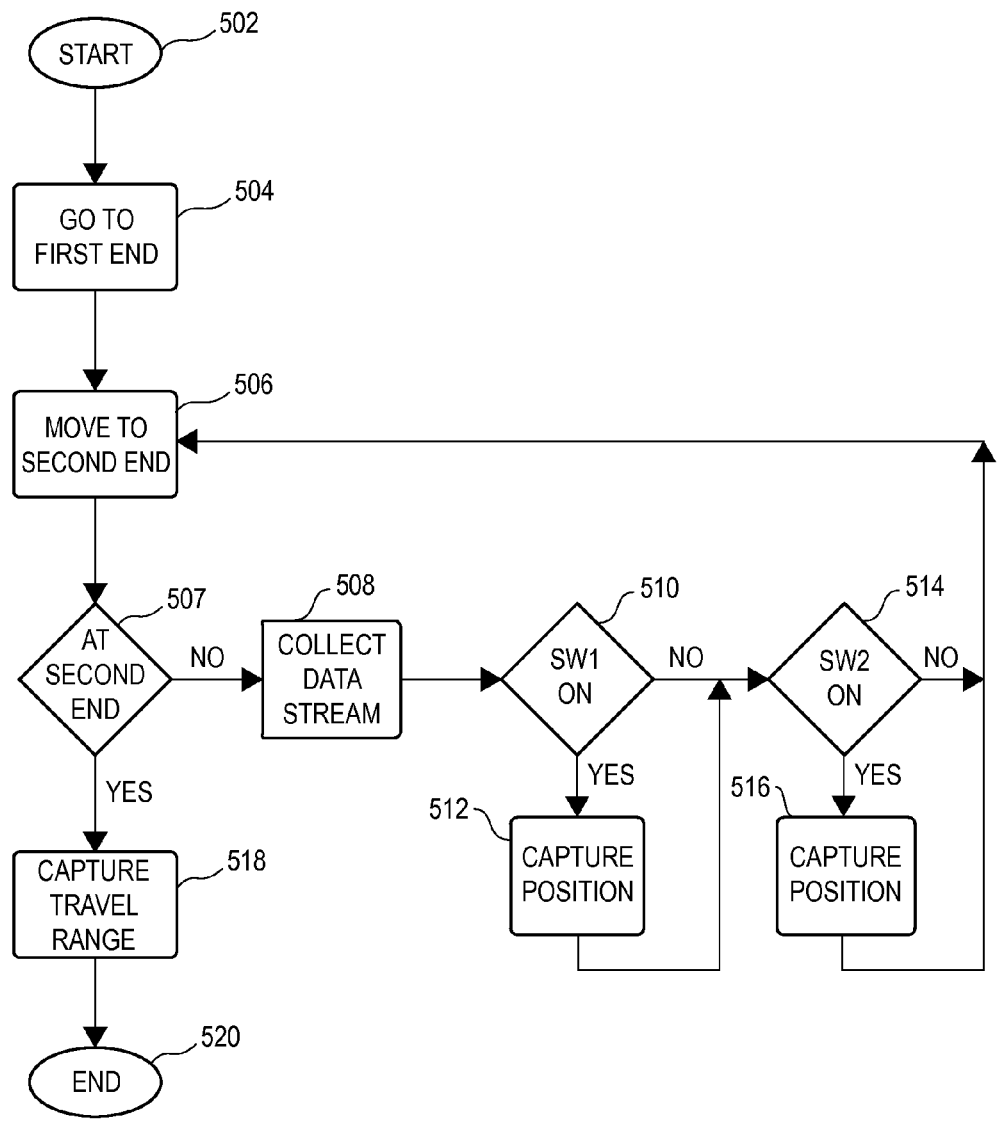
FIG. 5 is a flow chart illustrating an exemplary routine for establishing a baseline set of values for a motion axis in accordance with some embodiments.

There are instances where a motor may slip, an axis may have wearing components, sensor and/or feedback devices may fail, slip, or move, or an axis may be serviced without being properly calibrated prior to use. Any of these and other problems constitute safety hazards and may cause a mistreatment or undesirable machine shutdown. In some embodiments of the disclosure, a method of detecting the health of a motion axis is provided in which existing or potential problems can be identified, and warning or failure notifications may be generated. FIG. 4 is a flow chart illustrating the general steps of a method for detecting the health of a motion axis. According to the method, a baseline set of values of a motion axis is provided to a controller (step 402). The baseline set of values may include a general indicator of an electrical parameter of the motor such as the average, maximum, minimum, or standard deviation of the motor current etc. when the motor moves in a certain range. It is also possible to have a complete record of the readings throughout the range of motion and have this as an entire baseline signature or pattern. In situations where a motion axis includes hardstops and/or limit switches, the baseline values may also include the locations of hardstops, the locations of the limit switches relative to a hardstop, and the distances between the limit switches and/or between the hardstops. The baseline values can be determined when the axis is built or calibrated. To detect or monitor the health of the motion axis, data on the motor's electrical parameters, the locations of the limit switches, and/or the locations of hardstops are periodically collected (step 404). Analysis on the collected data may be performed in which any deviation from the baseline values or baseline signature or pattern may be calculated (step 406). Based on the magnitude of the calculated deviation, a health problem or fault may be identified, and warning or failure notifications may be generated FIG. 5 is a flow chart illustrating the exemplary steps of a process for obtaining baseline values of a motion axis. The process may start (502) by moving the axis to a first end (504). The first end may be a hardstop and a hardstop homing routine may be performed. In particular, the homing routine may be performed by monitoring an electrical parameter of the motor such as the motor current or back EMF etc. as the axis moves toward the first hardstop. Once the motor current reaches or exceeds a given value or threshold for a given duration of time, or once the back EMF drops to or below a given value or threshold for a given duration of time, the axis position is captured and the feedback device is reset. A home or zero position is defined based on the captured position of the feedback device. Alternatively, a homing routine may be performed by monitoring the motor velocity as the axis moves toward the first hardstop. Once the motor velocity falls to or below a given value for a given duration of time, the axis position is captured and a home or zero position is defined based on the captured position of the feedback device. The homing routine may also be performed by monitoring a secondary feedback device coupled to the load. When the axis moves toward the first hardstop the secondary feedback device is monitored. When the secondary feedback registers no motion for a given period of time, the axis position is captured and the feedback device is reset. U.S. application Ser. No. 12/641,538 filed Dec. 18, 2009 describes a method of homing and establishing reference frames for motion axes, the disclosure of which is incorporated herein by reference in its entirety.

Once a home or zero position is established, the axis may be commanded to move to a next position. For example, the axis may move in an opposite direction to a second end (506). In a certain range of the motion before the axis arrives at the second end or throughout the full motion, data on the motor's electrical parameter such as the motor's current may be collected (508). The motor's electrical parameter may generally be maintained at a relatively constant magnitude during the certain range of motion before the axis hits a hardstop. There may be variations on the magnitude due to the non-uniform friction of the axis components or any motor or feedback nonlinearities, providing a unique signature or pattern of the motor's electrical parameter. The pattern of the motor's electrical parameter may include a series of values or indicators including such as e.g. a maximum, a minimum, an average, and a standard deviation of the electrical parameter in the certain range of motion. The maximum, minimum, average, and standard deviation may be referred to as the indicators of the motor's electrical parameter in this disclosure. The data stream collected in the certain range of motion may be analyzed to obtain the pattern or signature of the motion axis, which may be stored and used in the health detection routine to be described in greater detail below.

An axis may optionally include one or more limit switches located near the hardstops. For example, a motion axis may include a first limit switch adjacent to a first hardstop and a second limit switch adjacent to a second hardstop. The limit switches, when triggered, may signal the controller that the axis is approaching to a hardstop. The controller may then reduces the axis speed and lower the peak torque capacity of the motor to avoid collision damage to the axis and increase positioning accuracy. During the motion of the axis to the second end, if at step 510 the first limit switch is triggered, the position of the axis may be captured as a baseline value for future comparison (512). If at step 514 the second limit switch is triggered, the position of the axis may be captured as a baseline value for future comparison (516).

The second end may be a hardstop and a routine similar to the first hardstop homing routine may be performed (507). In particular, the motor's electrical parameter or the motor feedback device, or the load feedback device may be monitored as the axis moves to the second hardstop. Once the motor current reaches or exceeds a given value for a given duration of time, or once the motor or load velocity falls to or below a given value for a given duration of time, the controller may capture the second end position (518) and the baseline routine is completed (520).

Figure 6:
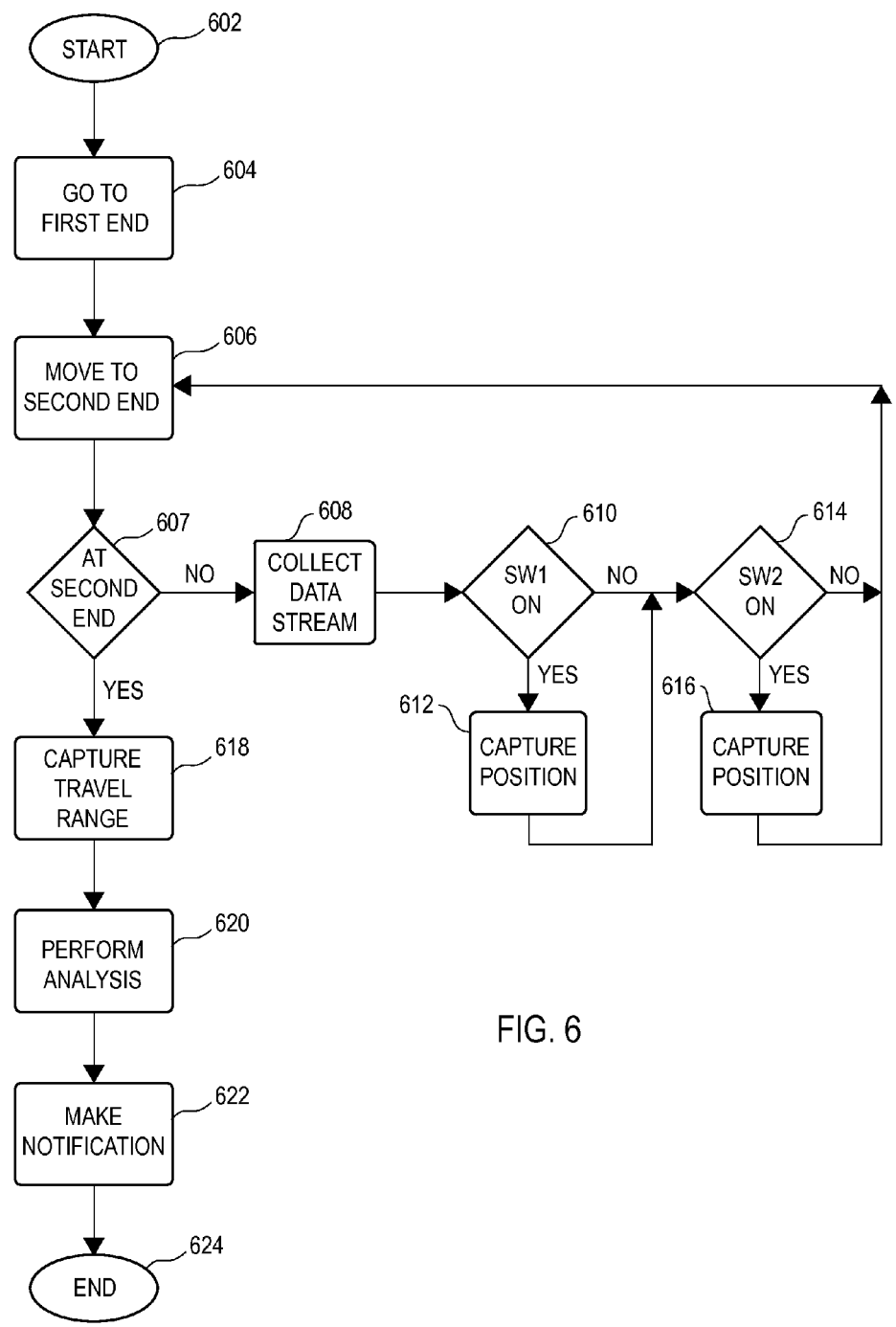
FIG. 6 is a flow chart illustrating an exemplary routine for detecting the health of a motion axis in accordance with some embodiments.

FIG. 6 is a flow chart illustrating exemplary steps of a routine for detecting the health of a motion axis. Similar to the baseline routine illustrated in FIG. 5, the health detection routine may start (602) by moving the axis to a first end such as a hardstop to perform a hardstop homing routine (604). Once a home or zero position is established, the axis may be commanded to move in an opposite direction to a second end (606). In a certain range of the motion or throughout the full motion, data on the motor's electrical parameter such as the motor's current may be collected (608), providing a pattern of the motor's electrical parameter including a series of values, including such as e.g. the maximum, minimum, average, and standard deviation of the motor's current. During the motion of the axis to the second end, if at step 610 the first limit switch is triggered, the position of the axis may be captured and recorded (612). If at step 614 the second limit switch is triggered, the position of the axis may be captured and recorded (616). The second end (607) may be a hardstop, and a routine similar to the first hardstop homing routine may be performed to capture and record the second end position (618). The above steps may be performed repeatedly or periodically at any time interval such as daily, weekly, or monthly. The data collected in each health detection routine may be stored for analysis using e.g. statistics calculations, trend analysis, or other techniques known in the art.

Figure 13:
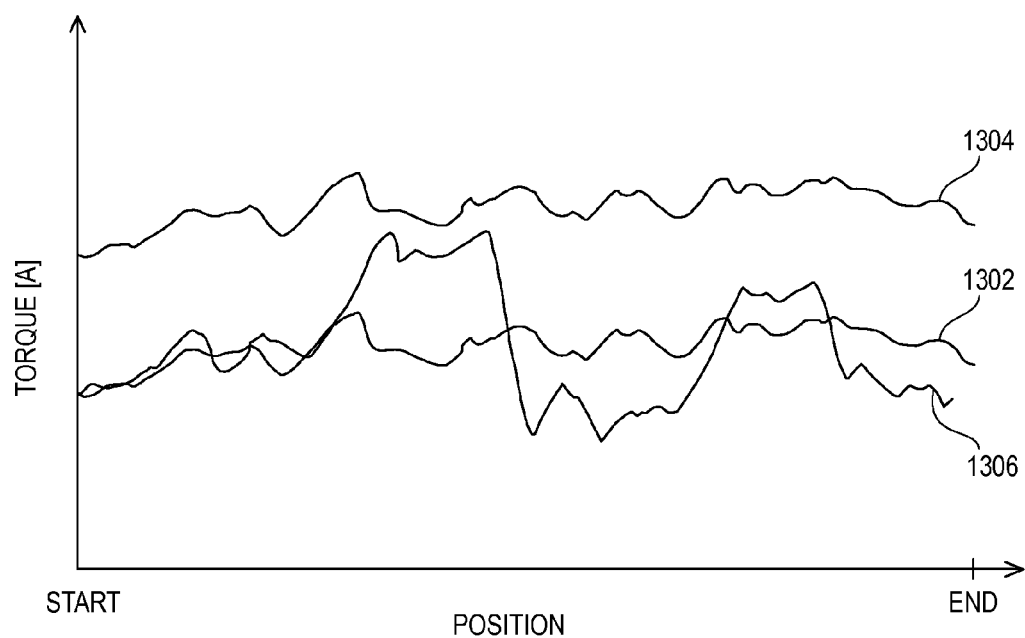
FIG. 13 shows schematic graphs demonstrating magnitude change patterns of the current of a motor in a baseline routine and a check-up routine for a motion axis.

Analysis may be performed at step 620. For example, one or more indicators of a motor's electrical parameter obtained in the health detection routines may be compared with one or more baseline value established in the baseline routine. For example, the pattern of the motor's current obtained in a check-up routine may be compared with the signature baseline values obtained in the routine illustrated in FIG. 5. FIG. 13 schematically shows an exemplary analysis. Graph 1302 represents an exemplary magnitude change pattern of the current of a motor moving in a certain range during a baseline routine, providing a series of repeatable values including such as the average, maximum, minimum, or standard deviation of the motor current etc. in the travel range. Graphs 1304, 1306 represent exemplary magnitude change patterns of the motor's current in check-up routines. If the magnitude change pattern of the current in a check-up routine substantially repeats the pattern of graph 1302, as illustrated by graph 1304, it may be an indication that the axis functions properly. If the magnitude change pattern of the current in a check-up routine deviates from the pattern of graph 1302, as illustrated by graph 1306, it may be an indication that the axis does not function properly or some faults exist. Graphs 1302 and 1304 are shown spaced apart for facilitating clarity. In reality, a portion or a significant portion of graphs 1302 and 1304 may be superimposed.

The positions of the hardstops or limit switches captured in the health detection routines may be compared to their corresponding baseline values obtained in the baseline routine. Alternatively, the distance between the limit switches or the travel range of the motion axis may be calculated based on the data collected in the health detection routines, and compared with their corresponding baseline values. During the analysis, any deviation from the baseline values or baseline signature or pattern may be calculated. If the magnitude of the deviation exceeds or falls below a predetermined threshold, a warning or failure notification may be generated and provided to e.g. an operator (622). The routine may end at step 624.

Figure 7:
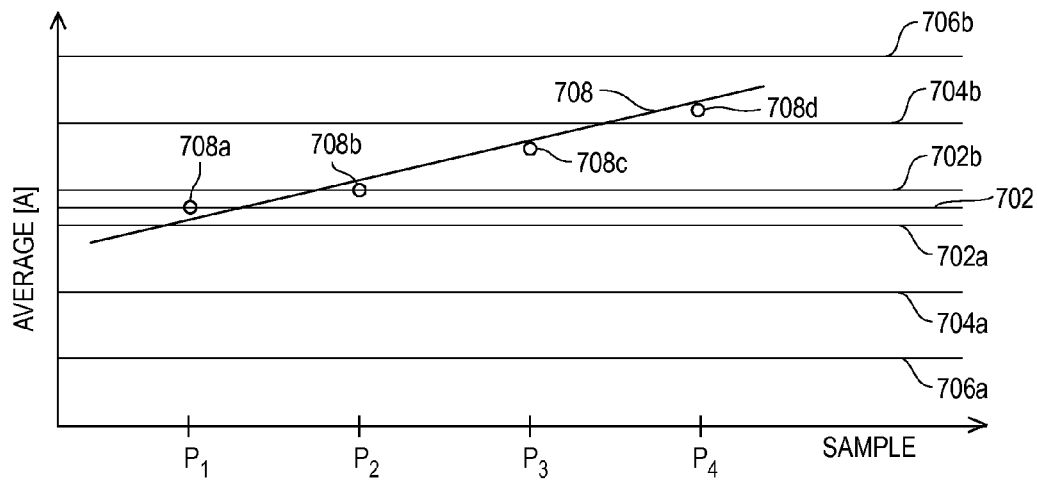
FIG. 7 is a schematic graph illustrating the magnitude change pattern of the average of a motor's torque in some health detection routines in accordance with some embodiments.

FIGS. 7-12 are graphs illustrating exemplary analyses of the data collected in the health detection routines. In FIG. 7, the average values of the motor's current (vertical axis) collected in the health detection routines (horizontal axis) are graphed. Line 702 represents a baseline value for the average of the motor's current established when the axis is built or calibrated using a baseline routine described above. For accuracy, a plurality of baseline routines may be performed and the baseline values for the average of the motor's current may vary in an acceptable range, as shown between lines 702a, 702b. Lines 704a, 704b may represent predetermined thresholds above or below which a warning notification may be generated for the motion axis. Lines 706a, 706b may represent predetermined thresholds above or below which a failure notification may be generated and the machine may shutdown. Reference numbers 708a, 708b, 708c, 708d represent the average values of the motor's current obtained based on the data collected in the health detection routines. By way of example, if the average value of the motor's current in a health detection routine falls within the range between lines 702a and 702b, it may be an indication that the motion axis functions properly. Conversely, if the average value of the motor's current in a health detection routine deviates from the range between lines 702a and 702b, it may be an indication that the motion axis does not functions properly. A trend analysis may be performed. For example, a line 708 approximately connecting the average values 708a, 708b, 708c, and 708d may provide indications of the health of the motion axis. A service may be called based on the trend analysis before the axis malfunctions. This may increase the up-time of the axis and prevent unexpected shutdown.

Figure 8:
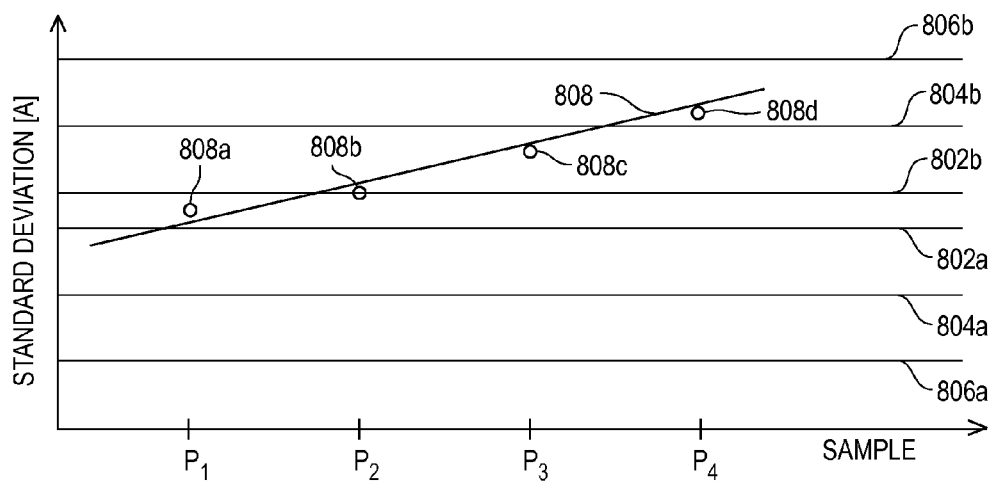
FIG. 8 is a schematic graph illustrating the magnitude change pattern of the standard deviation of a motor's torque in some health detection routines in accordance with some embodiments.
Figure 9:
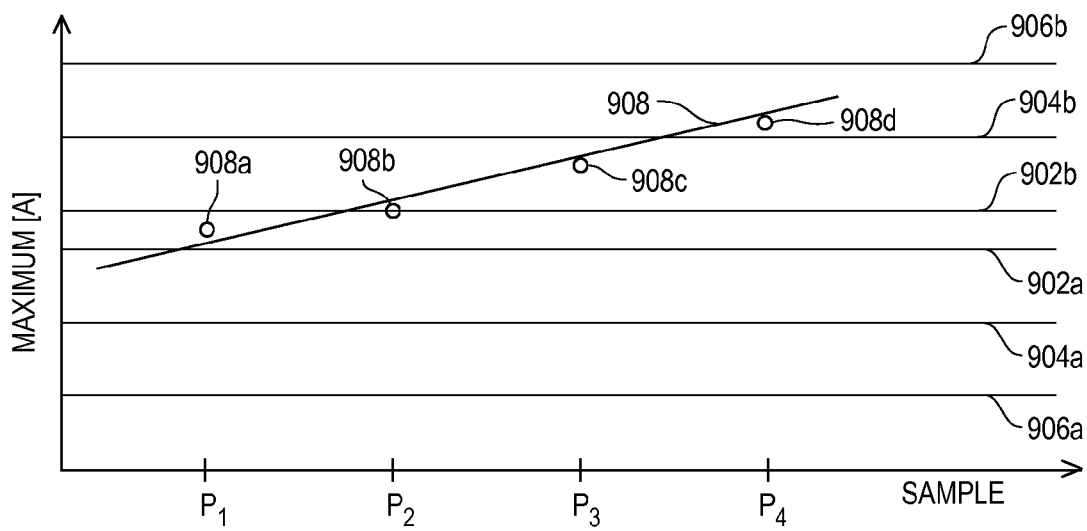
FIG. 9 is a schematic graph illustrating the magnitude change pattern of the maximum of a motor's torque in some health detection routines in accordance with some embodiments.
Figure 10:
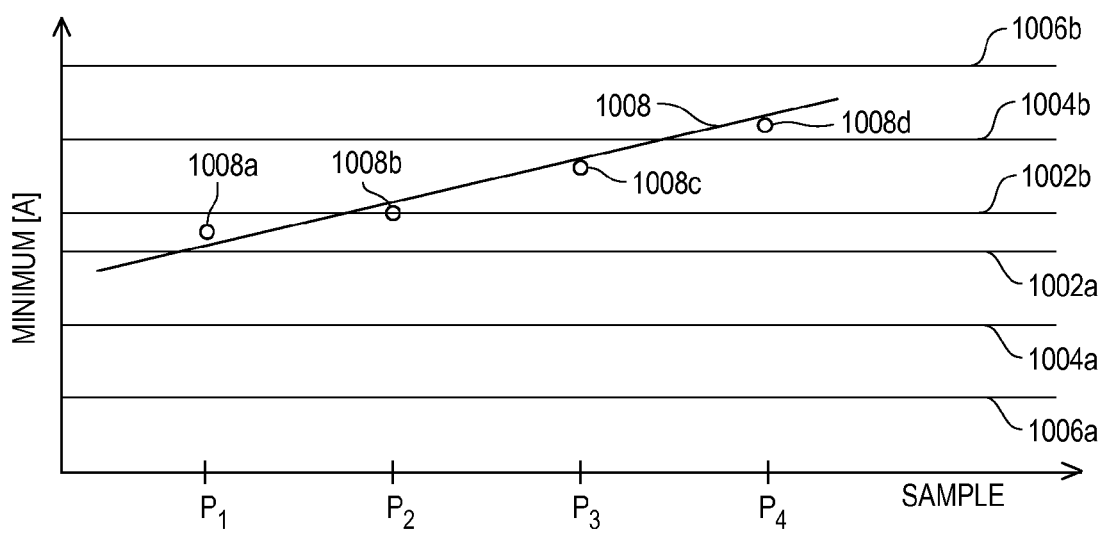
FIG. 10 is a schematic graph illustrating the magnitude change pattern of the minimum of a motor's torque in some health detection routines in accordance with some embodiments.

In FIG. 8, the standard deviations of the motor's current (vertical axis) collected in the health detection routines (horizontal axis) are graphed. Lines 802a, 802b define a normal range of baseline values of the standard deviations established when the axis is built or calibrated. Lines 804a, 804b may represent predetermined thresholds above or below which a warning notification may be generated. Lines 806a, 806b may represent predetermined thresholds above or below which a failure notification may be generated. Reference numbers 808a, 808b, 808c, 808d represent the standard deviation values obtained based on the data collected in the health detection routines. In FIG. 9, the maximal value of the motor's current (vertical axis) collected in the health detection routines (horizontal axis) are graphed. Lines 902a, 902b define a normal range of the baseline values of the maximum established when the axis is built or calibrated. Lines 904a, 904b may represent threshold values above or below which a warning notification may be generated. Lines 906a, 906b may represent threshold values above or below which a failure notification may be generated. Reference numbers 908a, 908b, 908c, 908d represent the maximal values obtained in the health detection routines. In FIG. 10, the minimal value of the motor's current (vertical axis) collected in the health detection routines (horizontal axis) are graphed. Lines 1002a, 1002b define a normal range of the baseline values of the minimum established when the axis is built or calibrated. Lines 1004a, 1004b may represent predetermined thresholds above or below which a warning notification may be generated. Lines 1006a, 1006b may represent predetermined thresholds above or below which a failure notification may be generated. Reference numbers 1008a, 1008b, 1008c, 1008d represent the minimal values collected in the health detection routines. Similar to the analysis of FIG. 7, if the standard deviation value in a health detection routine is within the normal range defined by lines 802a and 802b shown in FIG. 8, or if the maximal value in a health detection routine is within the normal range defined by lines 902a and 902b shown in FIG. 9, or if the minimal value in a health detection routine is within the normal range defined by lines 1002a and 1002b shown in FIG. 10, it may indicate that the motion axis functions properly. Conversely, if the standard deviation value, or the maximal value, or the minimal value in a health detection routine deviates from the normal ranges, it may indicate that the motion axis does not function properly. A trend analysis may be performed to determine or predict the health of the motion axis. A service may be called based on the trend analysis before the axis malfunctions.

Figure 11:
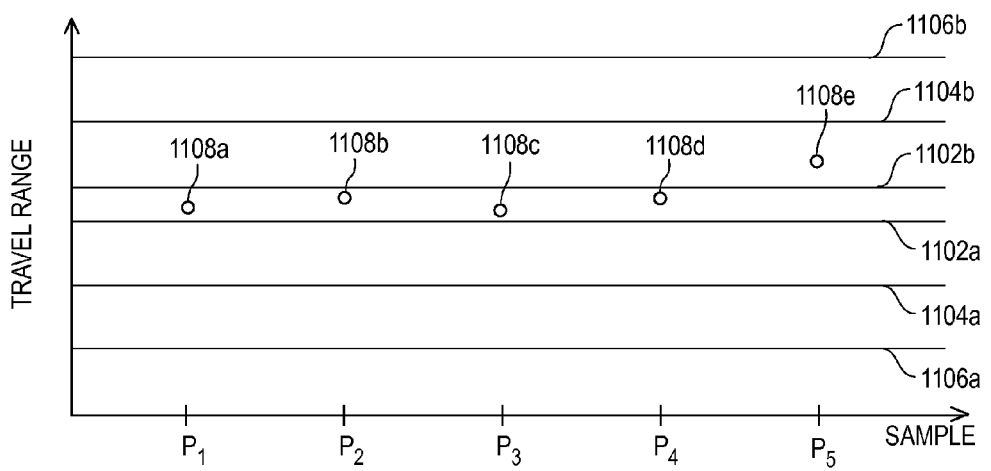
FIG. 11 is a schematic graph illustrating the magnitude change pattern of the travel range of a motion axis in some health detection routines in accordance with some embodiments.
Figure 12:
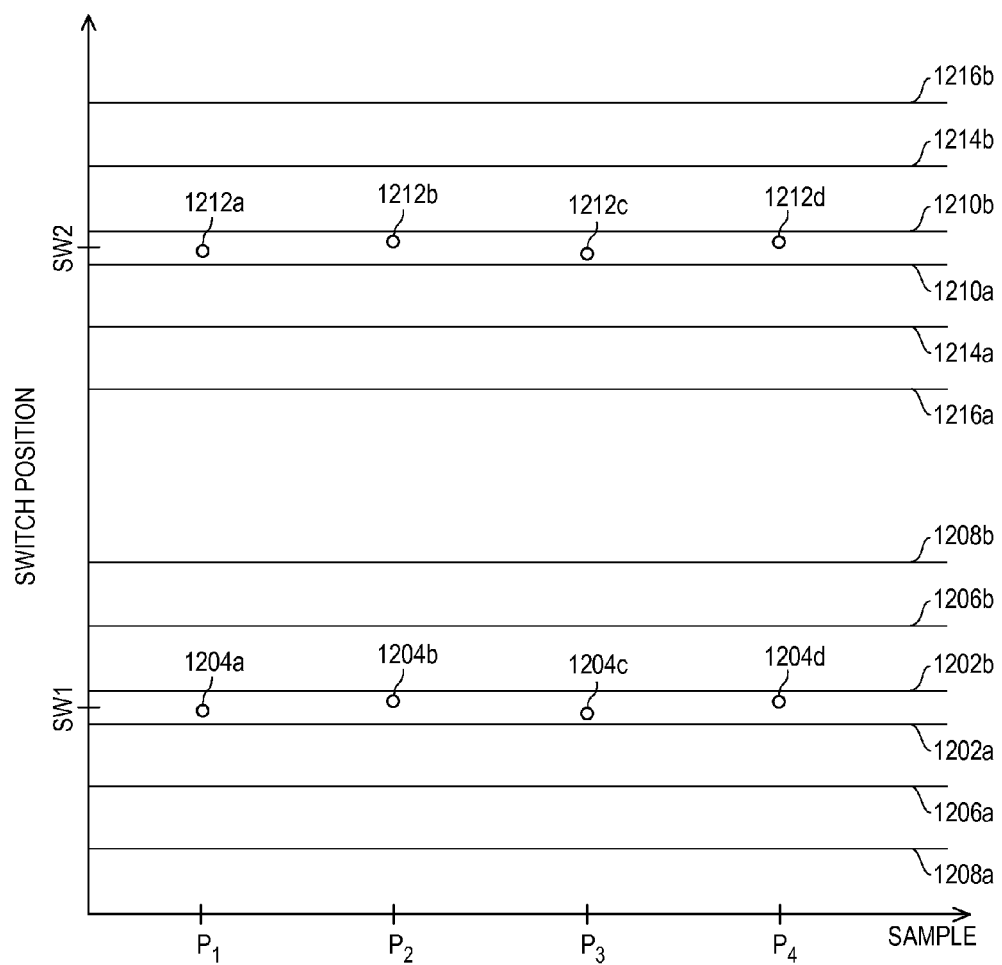
FIG. 12 is a schematic graph illustrating the magnitude change pattern of the positions of limit switches in a motion axis in some health detection routines in accordance with some embodiments.

FIGS. 11-12 provide additional exemplary analyses of the data collected in the health detection routines. In FIG. 11, the travel range of the motion axis (vertical axis) obtained in the health detection routines (horizontal axis) are graphed. Lines 1102a, 1102b define a normal range of baseline values for the travel range established when the axis is built or calibrated. Reference numbers 1108a, 1108b, 1108c, 1108d, 1108e represent the travel range values obtained in the health detection routines. If the value of a travel range in a health detection routine is within the normal range between lines 1102a and 1102b shown in FIG. 11, it may be an indication that the motion axis functions properly. Conversely, if the value of a travel range deviates from the normal ranges, it may be an indication that the motion axis does not function properly. Lines 1104a, 1104b may represent predetermined thresholds above or below which a warning notification may be generated. Lines 1106a, 1106b may represent predetermined thresholds above or below which a failure notification may be generated.

In FIG. 12, the locations of the limit switches (vertical axis) obtained in the health detection routines (horizontal axis) are graphed. Lines 1202a, 1202b define a normal range of the baseline values for the first limit switch, and lines 1210a, 1210b define a normal range of baseline values for the second limit switch established when the axis is built or calibrated. Reference numbers 1204a, 1204b, 1204c, 1204d represent the location values for the first limit switch, and reference numbers 1212a, 1212b, 1212c, 1212d represent the location values for the second limit switch collected in the health detection routines. Similarly, if the location value in a health detection routine falls within the normal range between lines 1202a and 1202b, or between 1210a and 1210b, it may be an indication that the motion axis functions properly. Conversely, if the location value deviates from the normal ranges, it may be an indication that the motion axis does not function properly. Lines 1206a, 1206b may represent predetermined thresholds for the first limit switch above or below which a warning notification may be generated. Lines 1208a, 1208b may represent predetermined thresholds for the first limit switch above or below which a failure notification may be generated. Lines 1214a, 1214b may represent predetermined thresholds for the second limit switch above or below which a warning notification may be generated. Lines 1216a, 1216b may represent predetermined thresholds for the second limit switch above or below which a failure notification may be generated. A trend analysis may be performed to diagnose any potential problems.

A method for detecting the health of motion axes in a radiation system has been described. Those skilled in the art will appreciate that various other modifications may be made within the spirit and scope of the invention. All these or other variations and modifications are contemplated by the inventors and within the scope of the invention.

What is claimed is:

1. A method comprising:
providing a linear accelerator system comprising a motion axis including a motor operable to move a load between a first end and a second end, wherein the first and second ends are a hardstop,
performing a homing routine using the first end to establish a reference position;
driving the motor to move the load from the first end to the second end;
collecting data on position of the second end,
calculating a distance between the first and second ends;
comparing the calculated distance with a provided value or range indicative of absence of a fault of the axis; and
detecting presence or absence of a fault of the motion axis using the comparison of the calculated distance with the provided value or range;
wherein the homing routine comprises:
driving the motor to move the load toward the first end;
monitoring an electrical parameter of the motor which reaches or exceeds a determined value when at least a portion of the load contacts the first end; and
defining the reference position for the motion axis when the monitored electrical parameter reaches or exceed the determined value.

2. The method of claim 1 wherein the motion axis further comprises a first limit switch adjacent to the first hardstop and/or a second limit switch adjacent to the second hardstop, and the method further comprises the steps of collecting data on location of the first and/or second limit switch with respect to the reference position, comparing the collected location data with a provided location value or range indicative of absence of a fault of the axis, and detecting presence or absence of a fault of the motion axis using the comparison.

3. The method of claim 1 further comprising the steps of collecting data on an electrical parameter of the motor as the motor moves in a certain range between the first and second hardstops, determining at least one indicator of the electrical parameter, comparing the at least one indicator with a provided parameter value or range of values indicative of absence of a fault of the axis, and determining presence or absence of a fault of the motion of the axis using the comparison of the at least one indicator and the provided parameter value or range of values.

4. The method of claim 3 wherein said at least one indicator of the electrical parameter includes a maximum, a minimum, an average, and a standard deviation of the electrical parameter.

5. The method of claim 1 wherein the axis comprises a motor operable to move an energy switch assembly, a target assembly, a filter positioning device assembly, an ion chamber assembly, a collimation assembly in a direction, a treatment couch top, a treatment couch base, or a positioning device for imaging in a direction.

6. The method of claim 1 wherein the steps of performing a homing routine, driving the motor, collecting data, and calculating the distance between the first and second ends are repeated over a period of time to provide a plurality of the calculated distance over the period of time, and said method further comprising analyzing the plurality of the calculated distance, and detecting presence or absence of a fault of the motion axis using the analysis of the plurality of the calculated distance.

7. The method of claim 1 wherein the provided value or range of values is established in a baseline routine of the axis.

8. The method of claim 1 further comprising the step of generating a notification if the calculated distance deviates from the provided value or range.

9. A method comprising:
providing a linear accelerator system comprising a motion axis including a motor, a load coupled to the motor, a first end and a second end defining a travel range of the load,
providing a first magnitude change pattern of an electrical parameter of the motor in the travel range of the load between the first end and the second end of the motion axis, the first magnitude change pattern of the electrical parameter is indicative of absence of a fault of the motion axis, wherein the electrical parameter of the motor comprising current or back EMF of the motor;
driving the motor to move the load between the first and second ends;
collecting data on the electrical parameter of the motor when moving the load between the first and second ends;
generating a second magnitude change pattern of the electrical parameter of the motor in the travel range of the load between the first end and the second end of the motion axis using the collected data;
comparing the second magnitude change pattern with the first magnitude change pattern;
determining presence or absence of a fault of the motion axis using the comparison; and
generating a warning or failure notification if presence of a fault is determined.

10. The method of claim 9 wherein the motion axis comprises a motor operable to move an energy switch assembly, a target assembly, a filter positioning device assembly, an ion chamber assembly, or a collimation assembly in a direction.

11. The method of claim 9 wherein the motion axis comprises a motor operable to move a treatment couch top, a treatment couch base, or a positioning device for imaging in a direction.

12. The method of claim 9 wherein the steps of driving the motor, collecting data, generating a second magnitude change pattern, comparing the second magnitude change pattern with the first magnitude change pattern, and determining presence or absence of a fault are repeated over a period of time to provide a plurality of the second magnitude change patterns over the period of time, and said method further comprises the steps of analyzing the plurality of the second magnitude change patterns, and detecting presence or absence of a fault of the motion axis based on the analysis of the plurality of the second magnitude change patterns.

13. The method of claim 9 further comprising the step of generating a notification if the second magnitude change pattern deviates from the first magnitude change pattern.

14. The method of claim 9 wherein the first magnitude change pattern is established in a baseline routine of the motion axis.

15. The method of claim 9 wherein at least one of the first and second ends is a hardstop, and said method further comprises a homing routine using the at least one hardstop to establish a reference position.

16. The method of claim 15 further comprising the steps of collecting data on locations of the first and second ends with respect to the home position, calculating a distance between the first and second ends, comparing the calculated distance with a provided distance value or range indicative of absence of a fault of the axis, and detecting presence or absence of a fault of the motion axis based on the comparison.

17. The method of claim 15 wherein the motion axis further comprises a first limit switch adjacent to the first end and/or a second limit switch adjacent to the second end, and the method further comprises the steps of collecting data on location of the first and/or second limit switch with respect to the reference position, comparing the collected location data with a provided location value or range indicative of absence of a fault of the axis, and detecting presence or absence of a fault of the motion axis using the comparison.

* * * * *